United States Patent [19]

Houseman

[11] Patent Number: 5,245,192

[45] Date of Patent: Sep. 14, 1993

[54] SELECTIVE IONIZATION APPARATUS AND METHODS

[76] Inventor: Barton L. Houseman, 17 Galloway Ave., Cockeysville, Md. 21030

[21] Appl. No.: 771,422

[22] Filed: Oct. 7, 1991

[51] Int. Cl.$^5$ .............................................. H01J 37/08
[52] U.S. Cl. ................................ 250/423 R; 250/287; 250/423 F; 313/362.1
[58] Field of Search .......... 250/286, 287, 288, 423 R, 250/423 F, 424; 313/230, 362.1

[56] References Cited

U.S. PATENT DOCUMENTS

| | | | |
|---|---|---|---|
| 3,621,242 | 11/1971 | Ferguson et al. | 250/287 |
| 3,665,241 | 5/1972 | Spindt | 250/423 R |
| 3,852,595 | 12/1974 | Aberth | 250/423 F |
| 4,458,149 | 7/1984 | Muga | 250/287 |
| 4,677,295 | 6/1987 | Negra et al. | 250/423 F |
| 4,902,897 | 2/1990 | Iwamatsu | 250/423 R |
| 4,926,056 | 5/1990 | Spindt | 250/423 F |
| 5,026,997 | 6/1991 | Benveniste | 250/423 R |

*Primary Examiner*—Bruce C. Anderson

[57] ABSTRACT

A gaseous sample that is to be analyzed is passed through an array of fine slits whose edges are covered with electrodes of opposite polarities to which is applied a variable electric potential. The voltage between the electrodes is varied at a programmed rate, so that the gaseous molecules become selectively ionized according to their required ionization energies. Measurement of the ionization current as a function of the voltage between the electrodes yields information about the identities and concentrations of the molecular species that are present in the gas. This selective ionization at atmospheric pressure improves the selectivity and dynamic range of ion mobility spectrometers and is also applicable to mass spectrometry and to improved analyte detection in gas chromatography.

19 Claims, 2 Drawing Sheets

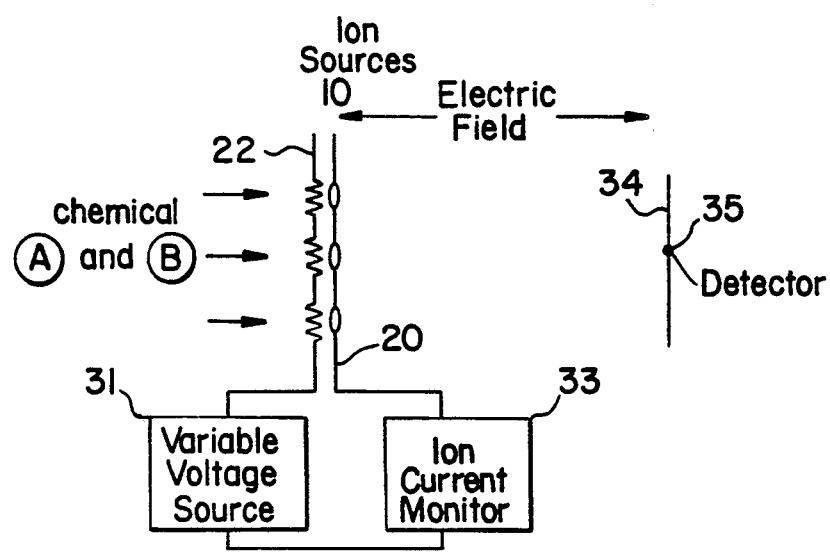
FIG. 5
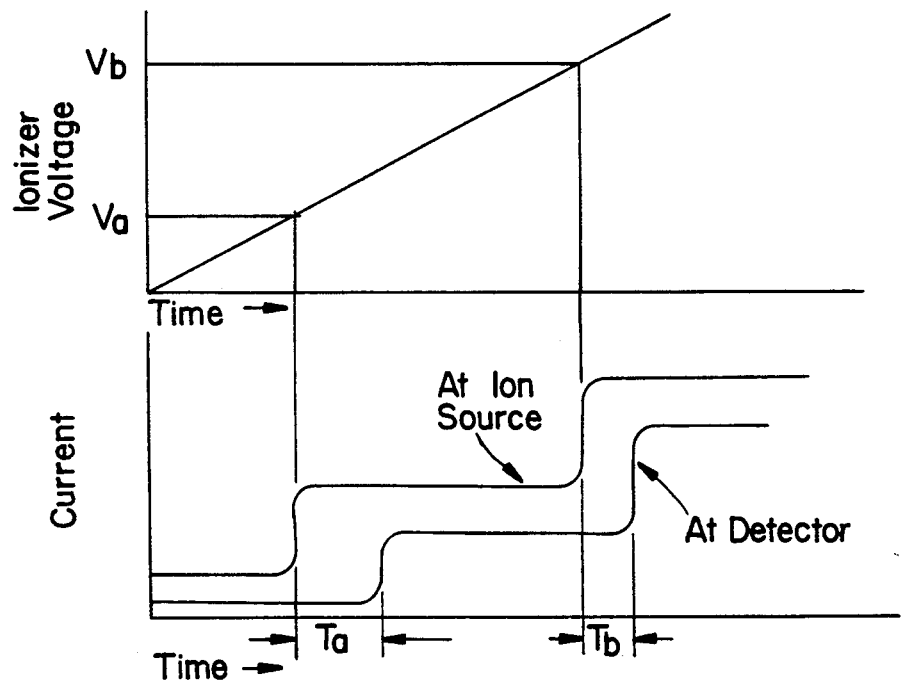
FIG. 6a
FIG. 6b
$V_a$ = Voltage at which ion A is formed
$V_b$ = Voltage at which ion B is formed
$T_a$ = Drift time for ion A
$T_b$ = Drift time for ion B

SELECTIVE IONIZATION APPARATUS AND METHODS

CONTRACTUAL ORIGIN OF THE INVENTION

The work that led to this invention was funded by the Chemical Research, Development and Engineering Center of the United States Army under Contract No. DAAA15-90-C-1069.

BACKGROUND OF THE INVENTION

This invention relates to selective ionization apparatus and methods, especially for use in mass spectrometry (MS), ion mobility spectrometry (IMS), gas chromatography (GC), and similar analytical technologies.

The term "ionization" is used herein to describe any process of ion formation in which molecules are converted into charged particles, whether by loss or gain of electrons or by loss or gain of ions.

Gas mixtures are most commonly analyzed at present by GC, MS or IMS. With GC, a special carrier gas and several minutes of processing time are usually required to produce analytical results. With MS, a vacuum of $10^{-4}$ torr or better is indispensable. Operation at atmospheric pressure and at high speed is achieved with MS, but the selectivity and dynamic range of IMS are much poorer than those obtained with either GC or MS.

It is an object of this invention to provide selective ionization apparatus and methods that will greatly improve the analytical selectivities especially of IMS devices and also of GC, MS and related instruments.

The term "analyte" as used herein refers to a substance of interest which is to be detected and whose concentration in a gaseous mixture is to be measured. It is an object of this invention to provide improved means of detecting and measuring very low concentrations of an analyte in air or in other gaseous mixtures in the presence of much higher concentrations of interfering species.

In current IMS technology, a gas sample enters an IMS assembly via a membrane at typically atmospheric pressure and at a selected temperature. The sample mixes with the gas inside a chamber that contains an ion source and an electric field. The ion source, Ni-63, produces a fixed number of ions per unit time. The chemicals in the chamber become ionized according to the laws of thermodynamics and are separated according to their charge polarity in the electric field.

In IMS instruments used for detection of chemical warfare (CW) agents, a common ionizable chemical, e.g., water vapor or acetone, is added to the gas to form reactant ions. These ions generate analyte ions by charge transfer reactions that take place with CW compounds, which often have the highest affinity for the charge. A small packet of the chemicals ionized in the source is allowed to enter a time-of-flight drift region where an electric field causes the ions in the packet to move. The ionized chemicals travel at different speeds (mobility) because they have slightly different weight, density, and molecular size. The ions are detected at the end of their flight using an electronic high-gain amplifier.

The IMS devices can detect CW substances and vapors of explosives or of illicit drugs in concentrations of 1 to 10 parts per billion by volume (ppbv). However, as the concentration of an analyte is increased, to say 100 to 500 ppbv, all of the reactant ions will have been used and no increase in output signal amplitude will be obtained (the analyte may form dimers and trimers). This leads to IMS systems with a limited dynamic range of measurable analyte concentrations.

The molecular weights of the singly-charged particles are typically between 50 and 500 atomic mass units, the path length is a few centimeters, the electric field is typically 100 to 200 volts/cm, and the resulting times-of-flight of the ionized analytes are typically 10 to 25 milliseconds. As the ion-molecules of a particular ionized species move along the time-of-flight path, they diffuse, and the resulting signal is considerably broader, in time, than the initial packet. The resulting signal has a resolution of between 20 and 50, where resolution is defined as the time width of each signal, measured at half the peak amplitude divided into the time of flight. The level of specificity (the ability to determine that a specific analyte is present because of a time-related output signal) is dependent on the charge affinity, ionization energy of the analyte, its adductive ion stability, its concentration, the concentration of reactant ions, as well as the affinity and concentrations of other compounds that are also trying to attract and capture the limited number of charges that are available. The analyte must have a unique velocity (mobility) in order to be detected at a unique time. These factors restrict the ability of IMS to specifically determine that the ionized species that is detected is a particular analyte.

Thus, the IMS hardware, as it is currently configured, has four important limitations:

1. Non-linear response to concentration: An analyte that produces a detectable IMS response at 5 ppbv can be expected, when exposed to concentrations of 50 ppbv and 100 ppbv, to produce responses that can hardly be distinguished from each other. The difference in minimum detection and signal saturation is ordinarily less than three decades for monomers.

2. Memory Effects: Exposure to a part-per million (ppm) concentration of an analyte can contaminate the IMS sensor, requiring hours or even days for clean-up and restoration of sensitivity.

3. Loss of sensitivity and selectivity due to charge stealing: Because the ionization process is competitive, the charges of the analyte ions can be captured by an interfering chemical that has a higher affinity for the charges. In general, IMS signals for mixtures are very difficult to deconvolute due to the interaction between different species in the source and during flight.

4. Loss of selectivity due to similar mobilities: The output signal will have unresolvable overlapping peaks when different ionized species with similar mobilities are in the same sample. Resolution of a diffusion-broadened peak limits the number of different mobilities that can be clearly isolated in a single detector scan.

In brief, present IMS devices utilize radioactive Ni-63 and an injected intermediate ionizable species to effect ionization in the gaseous samples that are to be analyzed. This favors the species that can be converted into the most stable ions while tending to mask other species. It also results, even for the favored species, in a saturation effect which limits the dynamic range of the concentrations that can be measured by IMS. It is therefore another object of this invention to provide a means of selectively ionizing analytes that yields ions of varying stabilities and over a wider range of analyte concentrations.

A microelectronic field ionizer that may be adaptable to selective ionization for IMS, MS and similar analytical technologies has been disclosed by C.A. Spindt in U.S. Pat. No. 4,926,056, issued on May 15, 1990. Spindt's field ionizer is made by a relatively elaborate procedure and allows a rather restricted flow of gas through its tiny orifices. It is therefore yet another object of this invention to provide a field ionizer that is relatively inexpensive and simple to produce and that permits a higher rate of gas flow per unit area of an ionizer array.

These and other objects of this invention will become apparent from the following description and appended claims.

SUMMARY OF THE INVENTION

This invention consists of selectively ionizing one or more analytes by means of an electric field of variable intensity.

To achieve ionization in an electric field, the sampled gas is passed between closely spaced electrodes. The voltage between the electrodes is varied at a programmed rate, so that the molecules in the gas become selectively ionized according to their required ionization energies. Measurement of the ionization current as a function of the voltage between the electrodes yields information about the molecular species that are present in the gas. The magnitudes of the changes in the ionization current yield a measure of the concentrations of different species.

In one preferred embodiment, this invention is used as a self-contained instrument which performs qualitative and quantitative analysis of active components in gas mixtures on the basis of the shape of the ionization current curve when plotted against applied voltage or of the derivative of this curve. Other embodiments include the use of this invention as an atmospheric pressure ionizer in MS, a detector in GC, and an ionizer in IMS. In each case, the fact that molecules with different ionization energies are ionized at different times means that species separations which are not achieved on the basis of time-of-flight in MS and IMS or on the basis of column mobility in GC may be possible with the additional separation step provided by this invention.

In the IMS application, the ion current is collected and measured at the end of the drift region by a detector. The magnitude of this detected ion current is proportional to the ionization current. The current-versus-time response is shaped similarly to that of the ionization current, differing only by a time delay, from which the ion mobility of each molecular species can be determined.

Two independent methods for the identification of the ionized chemical species in the sample are provided by this IMS configuration, thus greatly improving the resolution and selectivity of the device. In addition, this IMS configuration decreases the effect of interferences, extends the upper limit of measurable analyte concentrations, and provides a small improvement in sensitivity by the elimination of the shutter grid.

BRIEF DESCRIPTION OF THE DRAWINGS

The invention may be best explained with reference to the drawings in which:

FIG. 5 is a schematic diagram of the essential components of an IMS incorporating the present invention; and FIGS. 6a and 6b show the temporal changes in ion currents at an ion source and at an IMS detector for a ramping voltage across a field ionizer.

DESCRIPTION OF THE PREFERRED EMBODIMENTS

Figure 1:
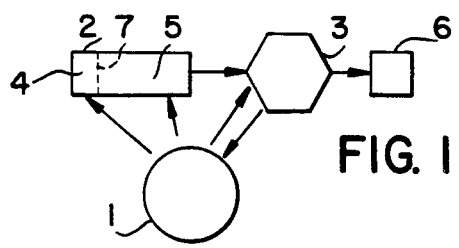
FIG. 1 is a block diagram of the main functional components of the invention.

As indicated in FIG. 1, the three common components of the embodiments of this invention are: a control means 1, a variable ionization means 2, and a signal receiving and processing means 3 (SRPM). The control means 1 controls the operations of the ionization means 2 and of the SRPM 3 and receives feedback from the SRPM. The ionization means 2 may comprise a sample introduction chamber 4 and an ion drift and detection compartment 5. The SRPM receives signals from the ionization means 2 and information about the ionization conditions from control means 1, processes the data, feeds back parts of the results to control means 1, and outputs the results into a receptacle 6, which may be a magnetic disc, a printer, a video monitor, or any other appropriate device.

Figure 2:
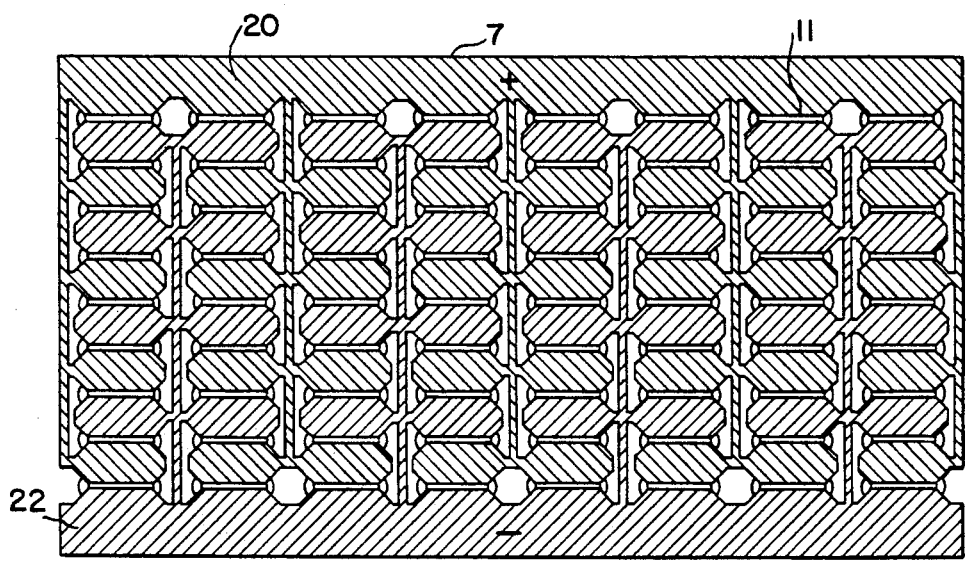
FIG. 2 is a rear view of an array of ionizing slits in one preferred embodiment of the invention.
Figure 3:
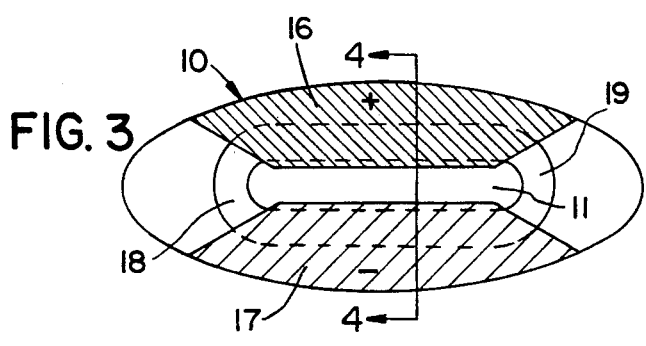
FIG. 3 is a magnified rear view of one of the ionizing slits of FIG. 2.
Figure 4:
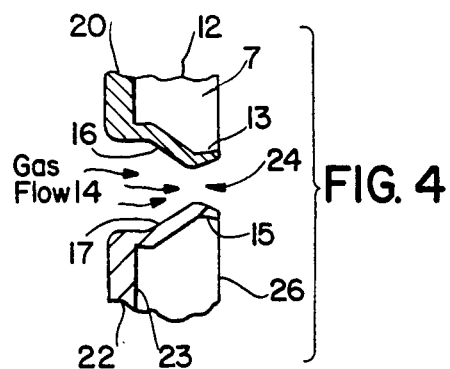
FIG. 4 is a cross-sectional view of the ionizing slit of FIG. 3.

In one preferred embodiment of the invention, the ionization chamber 4 comprises a planar array 7 of a multitude of ionizers 10 disposed as shown in FIG. 2. A magnified rear view of one of the ionizers 10 is shown in FIG. 3, and a cross-sectional view through section a—a' of FIG. 3 is shown in FIG. 4. As illustrated in FIG. 4, the planar array 7 comprises a planar substrate 12 made of an insulating material, such as alumina, quartz, plate glass, undoped silicon, or a photolithographically machinable polymer. A slit 11 in substrate 12, formed by a photolithographic etching technique, is tapered so as to have a wider opening at the back side, preferably 2–20 microns wide, and a narrower opening, preferably 0.1–1.0 micron wide, at the frontal face of substrate 12. The wider opening at the back side facilitates the flow of a gas 14 from the back to the front sides of substrate 12.

The opposite longitudinal edges 13 and 15 of slit 11 are covered by electrically conductive layers 16 and 17, preferably 0.2–0.4 micron thick. Layers 16 and 17 may comprise metals, such as platinum or gold, or if the substrate is glass or quartz, conductive tin oxide. Layers 16 and 17 are electrically insulated from each other, as indicated in FIG. 3, by the shorter metal-free edges 18 and 19 of slit 11. They each connect to interdigitated but non-contacting patterns 20 and 22 on the back side 23 of substrate 7, as shown by the differing hatchings of FIGS. 2, 3 and 4. The gap between layers 16 and 17 narrows down to 0.1–1.0 micron (preferably about 0.5 micron) near the front surface 26 of substrate 7, so that an electric potential of 100 V applied between these layers generates an electric field of about $10^6-10^7$ V/cm across the narrowest section of slit 11. To generate a higher electric field, e.g., of $10^8$ V/cm, the gas exit side 24 of slit 11 may be made narrower, e.g., only 0.1 micron wide, or the applied potential difference may be increased, e.g., to 300 V or even to about 1000 V.

As shown in FIG. 5, the variable ionization means 2 of FIG. 1 may comprise a variable voltage source 31 which serves to apply a variable voltage between layers 16 and 17, of FIGS. 3 and 4 or 20 and 22 of FIGS. 2, 4, and 5 an ion current monitor 33 which measures the current between these layers due to ionization of the gas passing through slits 11, and a detector 35 which measures the current due to ions reaching a counter-electrode 34 drifting in an electric field between the array of ion sources 10 and the electrode 34.

To distinguish between molecules having different ionization potentials, the voltage between layers 16 and 17 may be varied at a programmed rate, e.g., starting from a minimum value of about 10 V and increasing to a maximum value of about 1000 V and/or decreasing from the maximum to the minimum value, all within a minute fraction of a second. Such a programmed variation in voltage causes the most readily ionizable molecular species to yield an ionization current starting in the lower range of applied voltages, e.g., at 10–50 V. As the applied voltage rises, other less readily ionizable species begin to contribute to the ionization current.

A measurable ion current between layers 16 and 17 flows as soon as the ionization voltage of the most easily ionized species is reached. As the voltage continues to rise, the initial abrupt current increase stops and the current stays at a nearly constant value until the ionization voltage of a second species is reached. At this point another abrupt rise in ion current is followed by another plateau of a current-versus-time graph. This continues until all ionizable species have been ionized.

The currents due to two different species A and B whose ionization voltages at the exit 24 of slit 11 are $V_a$ and $V_b$, respectively, are shown in FIG. 6b, for a voltage between layers 16 and 17 that is ramping according to FIG. 6a. The current measured by the ion monitor 33 is illustrated by the upper curve of FIG. 6b and that measured by detector 35 is illustrated by the lower curve. The times at which species A and B ionize are the start times for the measurements of the ion mobilities or drift times $T_a$ and $T_b$, respectively. Since both the ionization voltages $V_a$, $V_b$ and the drift times $T_a$ and $T_b$ can be used to distinguish between different ions, the two independent measurements can be seen to yield far greater selectivity than could be obtained by one type of measurement (drift time or ionization voltage) alone.

In cases where the current increments following the start of ionization of a new species are not as sharp as those shown in FIG. 6b, improved accuracy in the measurement of the drift times $T_a$ and $T_b$ may be obtained from the time derivative of the current-versus-time graph.

Besides the information about the ionic species present in the sampled gas that is deducible from the drift times and ionization voltages, FIG. 6b also permits estimation of the concentrations of the species A and B from the differences in the heights of the current plateaus following each ionization step.

The array of ionizers of FIG. 2 should be preferably packed as densely as possible to facilitate the flow of ionized gas through the slits 10. For instance, if the spacing between nearest parallel slits is kept to 10 microns, as many as 1000 such slits can be formed over a 1-cm-wide substrate.

The afore-disclosed field ionizer offers several important advantages over the ionizers that are presently used in IMS devices. Direct ionization, without recourse to an intermediate ionizable reactant species, avoids complex ion-molecule reactions, reduces clustering effects and sensitivity to water vapor levels, eliminates saturation effects associated with limitations of reactant ions, and yields higher specifity for preferentially ionized organic compounds. Other advantages include relatively low cost and low power consumption and freedom from radio-active components.

It is also possible to use the selective ionizer as shown in FIG. 5, but without electrode-detector assembly 34, 35, as a self-contained instrument for gas analysis. In FIG. 6b, the ion source current curve alone provides information for analysis of gas mixtures. This configuration can also be used as a detector for GC (not shown) or as an atmospheric pressure ionizer for MS (not shown); in both cases additional selectivity can be attained with the selective ionizer.

There will now be obvious to those skilled in the art many modifications and variations of the afore-disclosed embodiment which, however, will remain within the scope of the invention if defined by the following claims.

We claim:

1. Apparatus for ionizing a component of a gaseous sample comprising an insulating substrate having a first side and a second side and a slit through said sides with two longitudinal edges, a first electrically conductive layer covering the first of said longitudinal edges and extending over one part of the surface of said first side, a second conductive layer covering the second of said longitudinal edges and extending over a second part of the surface of said first side, said first and second conductive layers being electrically insulated from each other, and means for applying an adjustable electric field between said first and second conductive layers so as to effectuate selective field ionization of said component.

2. The apparatus of claim 1, wherein said two longitudinal edges are parallel to each other and have a tapered portion which results in a separation between these edges that is wider on said first side than on said second side.

3. The apparatus of claim 2, wherein said first and second conductive layers are metallic.

4. The apparatus of claim 2, wherein said substrate comprises glass or quartz and one of said conductive layers comprises electrically conductive tin oxide.

5. The apparatus of claim 2, comprising a multitude of similar slits and interdigitated patterns of said first and second conductive layers that are electrically insulated from each other and are covering the respective first and second longitudinal edges of each slit.

6. The apparatus of claim 2, wherein the separation between said edges on said second side is about 20 microns or less.

7. The apparatus of claim 5, comprising means for varying said electric field with time, so as to selectively ionize an analyte, and means for monitoring the current between said layers due to ionization and hence deducing the analyte concentration in the gaseous sample.

8. The apparatus of claim 7, comprising means for applying a second electric field between said conductive layers and a counter-electrode that is situated at an opposite end of a drift region, detection means for measuring the current due to ions moving through said drift region end reaching said counter-electrode, and signal-processing means for deducing the identity and concentration of an analyte from the time-dependence of signals received by said monitoring means and by said detection means.

9. A method of identifying and measuring the concentration of an analyte in a gaseous mixture which comprises subjecting a sample of said mixture across a narrow slit to a ramping electric field that selectively ionizes the analyte, measuring the current due to field ionization of components of said mixture, and deducing the identity and concentration of the analyte from the dependence of said current on said electric field wherein said field is applied between electrodes that cover opposite longitudinal edges of said slit.

10. The method of claim 9 which comprises applying a time-varying electric field across a small opening so as to achieve selective field ionization of the analyte and passing a sample of mixture through said opening.

11. The method of claim 9, wherein said variable electric field is in the range of between $10^6$ V/cm and $10^8$ V/cm.

12. The method of claim 11 which comprises applying a second field between said electrodes and a counter-electrode that is situated at an opposite end of a drift region, measuring the current due to ions moving through said drift region and reaching said counter-electrode, and deducing the identity and concentration of the analyte from the time-dependence of the measured currents.

13. The method of claim 12 which comprises determining said time dependence with a mass spectrometer.

14. The method of claim 9, wherein said gaseous mixture is an eluent from a gas chromatograph.

15. Apparatus for ionizing a portion of a gaseous sample at ambient pressure which comprises means for passing said portion through a small slit having an inlet and an outlet, means for applying a time-varying electric field across said slit so as to effectuate selective field ionization of a component of said sample, and means for measuring the current due to ionization of said component near said outlet.

16. The apparatus of claim 15, wherein said variable electric field is in the range of between $10^6$ V/cm and $10^8$ V/cm.

17. The apparatus of claim 16, comprising means for applying a second electric field between said outlet and a counter-electrode that is situated at an opposite end of a drift region, detection means for measuring the current due to ions moving through said drift region and reaching said counter-electrode, and signal-processing means for deducing the identity and concentration of an analyte from the time-dependence of signals received by said ionization-current-measuring means and said detection means.

18. The apparatus of claim 17 in which said detection means comprises a mass spectrometer.

19. The apparatus of claim 15 in which said gaseous sample is an eluent from a gas chromatograph.

* * * * *